United States Patent [19]

Vinski et al.

[11] Patent Number: 5,776,443

[45] Date of Patent: Jul. 7, 1998

[54] HAIR CARE COMPOSITIONS

[75] Inventors: Paul Vinski, Danbury; Paul Edward Miner, Newtown, both of Conn.

[73] Assignee: Chesebrough-Pond's USA Co., Division of Conopco, Inc., Greenwich, Conn.

[21] Appl. No.: 616,949

[22] Filed: Mar. 18, 1996

[51] Int. Cl.$^6$ ................................................. A61K 7/075
[52] U.S. Cl. .................................... 424/70.12; 424/70.21; 424/70.22; 424/70.27; 510/121; 510/122
[58] Field of Search ............................ 424/70.12, 70.21, 424/70.11, DIG. 1, DIG. 2, 70.22, 70.27; 514/937; 510/119, 122, 121

[56] References Cited

U.S. PATENT DOCUMENTS

| | | | |
|---|---|---|---|
| 4,330,438 | 5/1982 | Dierassi et al. | 252/552 |
| 4,364,837 | 12/1982 | Pader . | |
| 4,656,043 | 4/1987 | Hawkins et al. | 424/70.19 |
| 4,741,855 | 5/1988 | Grote et al. . | |
| 4,900,545 | 2/1990 | Wisotzki et al. . | |
| 5,041,283 | 8/1991 | Kita et al. | 424/64 |
| 5,085,857 | 2/1992 | Reid et al. . | |
| 5,102,654 | 4/1992 | Castrogiovanni et al. . | |
| 5,118,507 | 6/1992 | Clement | 424/401 |
| 5,236,950 | 8/1993 | Aoyama et al. . | |
| 5,256,407 | 10/1993 | Gough . | |
| 5,350,572 | 9/1994 | Savaides et al. . | |
| 5,710,113 | 1/1998 | Wells | 510/122 |
| 5,714,135 | 2/1998 | Lee et al. | 424/70.11 |

FOREIGN PATENT DOCUMENTS

| | | |
|---|---|---|
| 0 686 386 | 12/1995 | European Pat. Off. . |
| 0 768 081 | 9/1996 | European Pat. Off. . |
| 42 15 501 | 5/1992 | Germany . |
| 4215501 | 10/1993 | Germany . |
| 19538094 | 10/1995 | Germany . |
| 61-236737 | 10/1986 | Japan . |
| 07 053 330 | 2/1995 | Japan . |
| 7-053330-A2 | 2/1995 | Japan . |
| 7-053331-A2 | 2/1995 | Japan . |

OTHER PUBLICATIONS

PCT International Search Report.
Chemical Abstracts, vol. 122, No. 22, 29 May 1995, Abstract No. 273768.
Seifen, Ole, Fette, Wachse, vol. 117, No. 10, 26 Jun. 1991, Augsburg (DE), pp. 379–384.
International Search Report.
Phytantriol Brochure (Hofmann LaRoche) Aug. 1, 1989.

*Primary Examiner*—Robert H. Harrison
*Attorney, Agent, or Firm*—Milton L. Honig

[57] ABSTRACT

A method and a hair care composition with stylability are provided for improving conditioning and stylability. The composition combines phytantriol and a silicone compound.

9 Claims, No Drawings

HAIR CARE COMPOSITIONS

BACKGROUND OF THE INVENTION

1. Field of the Invention

The invention relates to conditioning and styling hair compositions such as shampoos, styling gels and mousses.

2. The Related Art

Soil and sebum over time collect on the hair. An unattractive and dirty feel result. Regular treatment with shampoo removes built up soil and sebum.

Certain disadvantages attend the shampooing process. For instance, hair is left in a wet, tangled and unmanageable state. Combability is impaired.

Hair conditioners have been developed for post-shampoo application to improve combability and return hair to a manageable state. Application of a conditioner in a separate step is usually inconvenient.

More than a decade ago, dual action conditioning shampoos were introduced to the marketplace. An early entry was Dimension®, a product described in U.S. Pat. No. 4,364,837 (Pader), formulated with dimethicone and quaternary ammonium compounds (such as guar hydroxypropyltrimonium chloride) to assist the conditioning function. Pert Plus® 2-in-1, described in U.S. Pat. No. 4,741,855 (Grote et al.), employs combinations of a water-insoluble, nonvolatile silicone suspended by ethyleneglycol distearate or other esters of long chain fatty acids to achieve conditioning deposit of the silicone material onto the hair. Variants of Pert Plus® for permed hair list on their labels such further ingredients as polybutene, guar hydroxypropyl trimonium chloride and dihydrogenated tallowamidoethyl hydroxyethylmonium methosulfate.

Rave Plus® obtains conditioning effects through a combination of a silicone emulsion with guar hydroxypropyltrimonium chloride as described in U.S. Pat. No. 5,085,857 (Reid et al.).

Stylability is another desirable attribute for a hair product. U.S. Pat. No. 5,256,407 (Gough) achieves this attribute through incorporation of per-alk(en)yl hydrocarbon material, particularly polybutene. The highly hydrophobic nature of polybutene unfortunately presents compatibility difficulties and therefore limits its concentration level within a formulation.

Accordingly, it is an object of the present invention to provide a conditioning hair care composition with stylability features which overcomes problems with the known art.

Another object of the present invention is to provide a conditioning hair care composition with stylability features that can be applied to the hair in a single application.

These and other objects of the present invention will become more readily apparent from consideration of the following summary, detailed description and examples.

SUMMARY OF THE INVENTION

A hair care composition is provided that includes:

(i) from 0.001 to 1% by weight of phytantriol;
(ii) from 0.001 to 10% by weight of a silicone compound; and
(iii) a cosmetically acceptable carrier.

Particularly preferred are shampoos wherein the silicone is dimethicone and/or cyclomethicone. Cationic guar gums such as guar hydroxypropyltrimonium salt promote conditioning effectiveness. Enhanced performance is further achieved with the inclusion of keratin amino acids.

DETAILED DESCRIPTION OF THE INVENTION

Now it has been found that a combination of phytantriol and a silicone compound provides both conditioning and stylability to hair care compositions, especially shampoos. Phytantriol as known by its CTFA name is a hydrophobic branched triol chemically identified as 3,7,11,15-tetramethyl-1,2,3-hexadecanetriol. Commercially it is available from Hoffmann-La Roche, Inc., Nutley, N.J. For purposes of the present invention, the amount of phytantriol will range from 0.001 to 1%, preferably from 0.01 to 0.5%, optimally from 0.05 to 0.2% by weight.

Silicone compounds may be chosen from volatile and non-volatile silicone fluids. Volatile silicone fluids are preferably oils chosen from cyclic or linear polydimethyl siloxanes containing from 3 to 9, preferably from 4 to 5 silicon atoms.

Cyclomethicone is the most preferred cyclic volatile silicone. Linear volatile silicone oils generally have viscosities less than about 5 centistokes at 25° C. while cyclic fluids typically have viscosities of less than about 10 centistokes.

Nonvolatile silicone oils useful for the present invention include polyalkyl siloxanes, polyalkylaryl siloxanes and polyether siloxane copolymers. Non-volatile polyalkyl siloxanes useful herein include, for example, polydimethyl siloxanes with viscosities of from 5 to 100,000 centistokes at 25° C. Among the preferred non-volatile silicones are the polydimethyl siloxanes having viscosities from 10 to 400 centistokes at 25° C. These siloxanes are available, for example, from the General Electric Company as SF 1075 methyl phenyl fluid or from Dow Corning as 556 Cosmetic Grade Fluid.

The non-volatile polyalkylaryl siloxane fluids that may be used include, for example, polymethylphenylsiloxanes having viscosities of about 15 to 30,000 centistokes at 25° C.

Most preferred is dimethicone, especially an emulsion of dimethicone dispersed as particles within an aqueous phase. The preferred silicone emulsion of this variety is available from the Dow Corning Corporation under the trademark DC 1784.

Levels of these oils may range from 0.1 to 10%, preferably from 0.5 to 5%, optimally from 0.8 to 2.5% by weight.

Cationic guar gum may also be utilized as an adjunct conditioning agent. The CTFA name for a preferred guar gum is guar hydroxypropyltrimonium chloride. This material is available from Rhone-Poulenc under the trademark Jaguar®. Illustrative is Jaguar® C13S, having a low degree of substitution of cationic groups and a high viscosity. Other suitable varieties are Jaguar® C15, having a moderate degree of substitution and a low viscosity; Jaguar® C17 having a high degree of substitution and a high viscosity; and Jaguar® C16 which is a hydroxypropylated cationic guar derivative containing a low level of substituent groups as well as cationic quaternary ammonium groups. Also suitable is Jaguar® 162 which is a high transparency, medium viscosity guar having a low degree of substitution. Especially preferred is Jaguar® C13S.

Amounts of the cationic guar gum may range from 0.001 to 1%, preferably from 0.05 to 0.5%, optimally from 0.08 to 0.2% by weight.

Compositions of the present invention will necessarily include a cosmetically acceptable carrier. Generally this carrier will be water. Sometimes the carrier may be a propellant such as a hydrocarbon. Volatile solvents such as lower alcohols (e.g. ethanol) may be used instead of or in addition to water. Amounts of the carrier may range from 1 to 99.9% by weight, preferably from 20 to 99.5%, optimally from 40 to 80% by weight.

Hair care compositions of this invention are preferably in the form of shampoos but may also be in the form of conditioners, styling gels and mousses. These compositions are therefore amenable to liquid, gel and spray (aerosol and non-aerosol) formulations.

Amino acids may also be included in compositions of the present invention. Keratin type amino acids are available from Croda Inc. under the trademark Crotein HKP. Levels of this material may range from 0.01 to 2%, preferably from 0.1 to 1.5%, optimally from 0.3 to 0.8% by weight.

Compositions in accordance with the present invention when intended as shampoos will comprise one or more surfactants selected from anionic, nonionic, amphoteric, zwitterionic and cationic surfactants and mixtures thereof.

Suitable anionic surfactants are the alkyl sulphates, alkyl ether sulphates, alkaryl sulphonates, alkyl succinates, alkyl sulphosuccinates, N-alkoyl sarcosinates, alkyl phosphates, alkyl ether phosphates, alkyl ether carboxylates, and α-olefin sulphonates, especially their sodium, magnesium, ammonium and mono-, di- and tri-ethanolamine salts. The alkyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule, and preferably contain 2 to 3 ethylene oxide units per molecule.

Examples of further suitable anionic surfactants include sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

The nonionic surfactants suitable for use in shampoos of the invention may include condensation products of aliphatic ($C_8$–$C_{18}$) primary or secondary linear or branched-chain alcohols or phenols with alkylene oxides, usually ethylene oxide and generally 6–30 EO groups.

Other suitable nonionic surfactants include mono- or di-alkyl alkanolamides, alkyl polyglucosides and polyhydroxy fatty acid amides (e.g. methyl glucamides). Examples are coco mono- or di-ethanolamide, coco mono-isopropanolamide, and coco polyglucoside.

The amphoteric surfactants suitable for use in the invention may include alkyl amine oxides, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to 18 carbon atoms. Examples include lauryl amine oxide, cocodimethyl sulphopropyl betaine and, preferably, lauryl betaine, cocamidopropyl betaine and sodium cocamphopropionate.

Examples of cationic surfactants include: quaternary ammonium hydroxides and salts thereof, for example cetyl trimethylammonium chloride, stearyl dimethylbenzylammonium chloride, cetylpyridinium chloride, quaternium-5,-31,-18 and mixtures thereof.

The level of surfactant materials may range from 1 to 40%, preferably from 2 to 35%, optimally from 3 to 5% by weight of the composition.

Another ingredient that may advantageously be incorporated into the hair care compositions of the invention is a fatty alcohol material. The combined use of fatty alcohol material and cationic surfactant in conditioning compositions is believed to be especially advantageous, because this leads to the formation of a lamellar phase, wherein the cationic surfactant is dispersed. Preferred fatty alcohols contain from 8 to 22 carbon atoms, more preferably 16 to 20. Examples of preferred fatty alcohols are cetyl alcohol and stearyl alcohol. The level of fatty alcohol material may range from 0.1 to 10%, preferably from 7.5–9.5% by weight of the composition.

Also includable are minor amounts of other ingredients commonly found in hair care compositions, such as antibacterial agents, antidandruff agents (e.g. zinc pyridinethione or Octopirox®), foam boosters, perfumes, dyes, coloring agents, preservatives, viscosity modifiers, polymers, buffering agents, polyols and other moisturizing agents, herb extracts, mink oil or honey.

Opacifiers or pearlescers may also be formulated into compositions of the invention. Suitable are ethylene glycol esters of fatty acids having from about 16 to 22 carbon atoms. Preferred are the ethylene glycol stearates, both mono and distearate, but particularly the distearate. Most preferred, however, is titanium dioxide coated mica, commercially available as Timiron® MP1001.

Compositions of the invention in shampoo form are generally applied in an amount of from 1 to 50 mls, preferably from 3 to 5 mls to wet hair. After applying the shampoo the wet hair is worked to create a lather. The lather may be retained on the hand for a short time before rinsing, e.g. from 1 to 4 minutes, or may immediately be rinsed. The treatment may be repeated, if required.

The following examples will illustrate preferred embodiments within the scope of the present invention. These examples are solely for the purpose of illustration and are not to be construed as limitations of the present invention as many variations thereof are possible without departing from the purview and spirit of the invention.

EXAMPLES 1–4

Formulations illustrative of the present invention are listed under Table I. These Examples represent respectively Normal, Fine, Dry and Permed variations of shampoo.

TABLE I

| INGREDIENTS | EXAMPLES (WEIGHT %) | | | |
|---|---|---|---|---|
| | 1 | 2 | 3 | 4 |
| Sodium Lauryl Ether Sulphate (25% active) | 56.00 | 56.00 | 56.00 | 56.00 |
| Carbopol ® 980 (2% soln.) | 20.00 | 20.00 | 20.00 | 20.00 |
| Betaine (30% active) | 6.67 | 6.67 | 6.67 | 6.67 |
| DC 1784 (50% active) | 2.00 | 1.50 | 4.00 | 4.00 |
| Propylene Glycol | 0.50 | 0.50 | 0.50 | 0.50 |
| Fragrance | 0.60 | 0.60 | 0.60 | 0.60 |
| Sodium Chloride | 0.50 | 0.50 | 0.50 | 0.50 |
| Crotein HKP ® | 0.50 | 0.50 | 0.50 | 0.50 |
| NaOH | 0.45 | 0.45 | 0.45 | 0.45 |
| Timiron ® MP1001 | 0.20 | 0.20 | 0.20 | 0.20 |
| Phytantriol | 0.10 | 0.10 | 0.10 | 0.10 |
| Jaguar ® C13S | 0.10 | 0.10 | 0.20 | 0.20 |
| Glydant Plus ® | 0.10 | 0.10 | 0.10 | 0.10 |
| BHT | 0.05 | 0.05 | 0.05 | 0.05 |
| Panthenol | 0.00 | 0.00 | 0.00 | 0.10 |
| Water | balance | balance | balance | balance |

EXAMPLES 5–9

Examples of conditioner formulations are provided under Table II. The Examples respectively represent Normal, Fine, Dry, Permed and Intensive conditioners.

TABLE II

| INGREDIENTS | EXAMPLES (WEIGHT %) | | | | |
| --- | --- | --- | --- | --- | --- |
| | 5 | 6 | 7 | 8 | 9 |
| Cetearyl Alcohol | 3.75 | 3.50 | 3.75 | 3.75 | 4.75 |
| Cetyl Alcohol | 3.75 | 3.50 | 3.75 | 3.75 | 4.75 |
| Cetrimonium Chloride (29% active) | 3.45 | 3.45 | 4.31 | 4.65 | 3.45 |
| Paraffin | 1.25 | 1.25 | 1.25 | 1.25 | 1.25 |
| DC 1784 (50% active) | 1.00 | 0.50 | 1.50 | 2.50 | 3.00 |
| Stearyl Stearate | 0.50 | 0.00 | 0.50 | 0.50 | 0.00 |
| Crotein HKP ® | 0.50 | 0.50 | 0.50 | 0.50 | 0.50 |
| Fragrance | 0.60 | 0.60 | 0.60 | 0.60 | 0.60 |
| Glydant Plus ® | 0.10 | 0.10 | 0.10 | 0.10 | 0.10 |
| Phytantriol | 0.10 | 0.10 | 0.10 | 0.10 | 0.10 |
| BHT | 0.05 | 0.05 | 0.05 | 0.05 | 0.05 |
| Behenyl Trimonium Chloride (35% active) | 0.00 | 0.00 | 0.00 | 0.00 | 1.43 |
| Cetyl Palmitate | 0.00 | 0.50 | 0.00 | 0.00 | 0.50 |
| PEG 1450 | 0.00 | 0.10 | 0.00 | 0.00 | 0.00 |
| Panthenol | 0.00 | 0.00 | 0.00 | 0.00 | 0.50 |
| Water | balance | balance | balance | balance | balance |

EXAMPLE 10

This Example demonstrates the benefits of phytantriol and silicone oil combinations for improving the conditioning property of wet combing.

Chemically untreated European brown hair was formed into 6-inch long, 5-gram hair swatches. Each was bleached twice within 48 hours to represent chemically damaged hair. A sample size of 12 swatches was used for each shampoo treatment.

A shampoo base identical to the formula of Example 1 (absent DC 1784, Crotein HKP®, Timiron® MP1001 and Jaguar® C13S) was applied to the hair swatches in a treatment consisting of:

A one minute soak in 40° C. water

Shampoo for one minute

Rinse under running water for 30 seconds

Shampoo for one minute

Rinse under running water for 30 seconds

After rinsing, the combability of the swatches was evaluated.

Wet combability was measured using an INSTRON Universal Testing Instrument Model 4501, INSTRON Corporation, Canton, Mass. The instrument is a computer-controlled electromechanical device designed to measure force as a function of applied strain. A hair swatch was suspended from the instrument's load cell, while a comb attached to the instrument's moving crosshead passed through it at a speed of 5 cm/min. A computer collected the data and transformed it into the amount of work required to comb through the swatch. The data is presented in Table III.

TABLE III

| | Wet Combing Results | |
| --- | --- | --- |
| SAMPLE NO. | SHAMPOO TESTED | WORK (gm − cm) |
| 1 | Base | 1344 |
| 2 | Base + 0.05% phytantriol | 1021 |
| 3 | Base + 0.1% phytantriol | 988 |
| 4 | Base + 0.25% phytantriol | 836 |
| 5 | Base + 0.5% silicone | 1118 |
| 6 | Base + 0.05% phytantriol + 0.5% silicone | 848 |
| 7 | Base + 0.1% phytantriol + 0.5% silicone | 734 |
| 8 | Base + 0.25 phytantriol + 0.5% silicone | 648 |

A lower value for "work" indicates an improvement in wet combing, i.e., less effort to comb the hair. The standard deviation for all the samples was generally 10%. The results indicate that phytantriol assisted in reducing wet combing work and that increasing its level decreased the work. Silicone, as shown in Sample 5, also had an effect. The combinations of phytantriol and silicone have an exceptionally large effect upon enhancing wet combability.

Although the invention has been described with reference to specific Examples, it will be apparent to one skilled in the art that various modifications will be suggested, all of which are within the spirit and purview of this invention.

What is claimed is:

1. A hair care composition comprising:

(i) from 0.001 to 0.25% by weight of phytantriol;

(ii) from 0.001 to 10% by weight of a silicone compound; and (iii) from 20 to 99.9% by weight of water.

2. The composition according to claim 1 wherein the silicone compound is present as a silicone emulsion in water.

3. The composition according to claim 1 further comprising a cationic guar gum.

4. The composition according to claim 3 wherein the cationic guar gum is a guar hydroxypropyl trimonium salt.

5. The composition according to claim 1 further comprising from 0.001 to 1% by weight of amino acids.

6. The composition according to claim 1 wherein the silicone compound is selected from the group consisting of dimethicone and cyclomethicone.

7. A method for conditioning and styling hair comprising the steps of:

(a) applying a hair care composition to the hair comprising:

(i) from 0.001 to 0.25% by weight of phytantriol;

(ii) from 0.001 to 10% by weight of a silicone compound;

(iii) from 20 to 99.5% by weight of water; and (iv) from an effective amount to be surface active to 40% by weight of a surfactant;

(b) wetting the hair to create a lather;

(c) rinsing the lather from the wet hair; and (d) applying heat to the rinsed hair to achieve styling.

8. The method according to claim 7 wherein the surfactant is an anionic surfactant.

9. The method according to claim 8 wherein the anionic surfactant is a lauryl ether sulphate.

* * * * *

UNITED STATES PATENT AND TRADEMARK OFFICE
CERTIFICATE OF CORRECTION

PATENT NO. : 5,776,443
DATED : July 7, 1998
INVENTOR(S) : Vinski et al.

It is certified that error appears in the above-indentified patent and that said Letters Patent is hereby corrected as shown below:

On title page, item [75],
Inventor Section: Inventor's name, change "Paul Edward Miner"

to -- Philip Edward Miner -- .

Signed and Sealed this

Third Day of November, 1998

*Attest:*

BRUCE LEHMAN

*Attesting Officer*    Commissioner of Patents and Trademarks